(12) United States Patent
Kwak et al.

(10) Patent No.: US 11,345,881 B2
(45) Date of Patent: May 31, 2022

(54) NANOFIBER STRUCTURE FOR CELL CULTURE, METHOD FOR MANUFACTURING THE NANOFIBER STRUCTURE, AND CELL ANALYSIS DEVICE INCLUDING THE NANOFIBER STRUCTURE

(71) Applicant: Industry-Academic Cooperation Foundation of Ajou University, Suwon-si (KR)

(72) Inventors: Jong-Young Kwak, Suwon-si (KR); Young-Hun Jeong, Daegu (KR); Jeong-Hwa Kim, Yongin-si (KR); Tae-Eon Kim, Suwon-si (KR)

(73) Assignee: INDUSTRY-ACADEMIC COOPERATION FOUNDATION OF AJOU UNIVERSITY, Suwon-si (KR)

( * ) Notice: Subject to any disclaimer, the term of this patent is extended or adjusted under 35 U.S.C. 154(b) by 936 days.

(21) Appl. No.: 16/063,055

(22) PCT Filed: Dec. 8, 2016

(86) PCT No.: PCT/KR2016/014384
§ 371 (c)(1),
(2) Date: Jun. 15, 2018

(87) PCT Pub. No.: WO2017/105035
PCT Pub. Date: Jun. 22, 2017

(65) Prior Publication Data
US 2018/0362913 A1    Dec. 20, 2018

(30) Foreign Application Priority Data

Dec. 18, 2015 (KR) .................. 10-2015-0181611

(51) Int. Cl.
*C12M 1/12* (2006.01)
*C12M 1/00* (2006.01)
(Continued)

(52) U.S. Cl.
CPC ............ *C12M 25/14* (2013.01); *C12M 23/20* (2013.01); *C12M 23/34* (2013.01); *C12M 41/46* (2013.01);
(Continued)

(58) Field of Classification Search
CPC ...... C12M 23/20; C12M 25/14; C12M 23/34; C12M 41/46; C12N 5/0068;
(Continued)

(56) References Cited

U.S. PATENT DOCUMENTS 7,579,077 B2 * 8/2009 Dubrow ............. B01J 20/28007
424/422
2008/0233607 A1 * 9/2008 Yu ..................... B01L 3/502761
435/29

FOREIGN PATENT DOCUMENTS

KR       10-0753116 B1      8/2007
KR   10-2010-0000289 A      1/2010
(Continued)

OTHER PUBLICATIONS

Xie et al. Neurite Outgrowth on Electrospun Nanofibers with Uniaxial Alignment: The Effects of Fiber Density, Surface Coating, and Supporting Substrat. ACS Nano (2014), 8(2), 1878-1885. (Year: 2014).*

*Primary Examiner* — Sean C. Barron
(74) *Attorney, Agent, or Firm* — Vorys, Sater, Seymour and Pease LLP; Mih Suhn Koh

(57) ABSTRACT

The present disclosure relates to a nanofiber structure for cell culture, a method for manufacturing the structure, and a cell analysis device including the nanofiber structure for cell culture. The structure includes a cell culture layer made of nanofibers; and a spacer protruding upward from a surface of the cell culture layer, wherein the spacer divides a region on the cell culture layer into at least two culturing regions, wherein the spacer is made of the same nanofibers as the cell
(Continued)

culture layer and thus has a cell migration channel defined therein.

14 Claims, 9 Drawing Sheets

(51) Int. Cl.
    *C12M 1/34*     (2006.01)
    *C12N 5/00*     (2006.01)
    *C12N 5/09*     (2010.01)

(52) U.S. Cl.
    CPC .......... *C12N 5/0068* (2013.01); *C12N 5/0693* (2013.01); *C12N 2533/40* (2013.01); *C12N 2533/54* (2013.01); *C12N 2533/72* (2013.01); *C12N 2533/78* (2013.01); *C12N 2533/80* (2013.01); *C12N 2535/00* (2013.01)

(58) Field of Classification Search
    CPC .............. C12N 5/0693; C12N 2533/80; C12N 2533/40; C12N 2533/72; C12N 2535/00; C12N 2533/54; C12N 2533/07
    See application file for complete search history.

(56) References Cited

FOREIGN PATENT DOCUMENTS

| KR | 10-2012-0097948 A | 9/2012 |
|---|---|---|
| KR | 10-1446687 B1 | 10/2014 |
| KR | 10-1484996 B1 | 1/2015 |
| KR | 101484996 B1 * | 1/2015 |

* cited by examiner

[Figure 1]
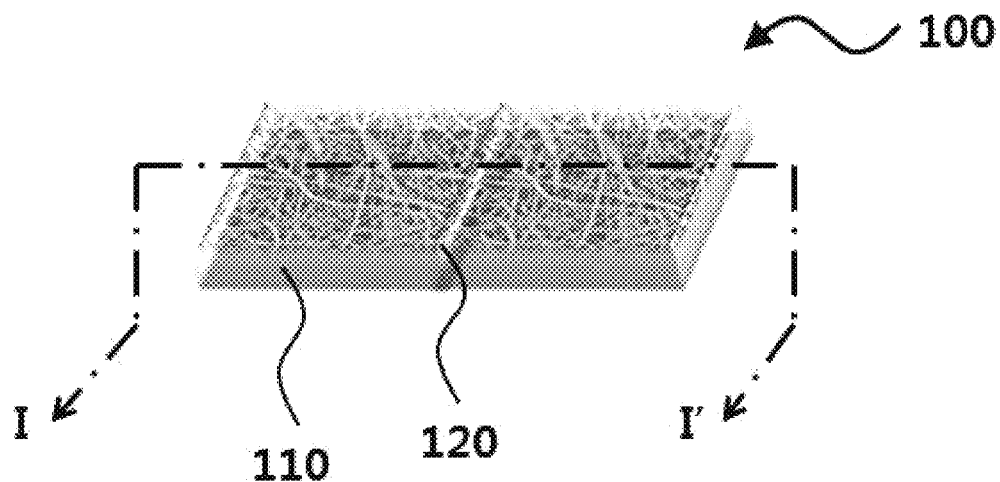
[Figure 2]
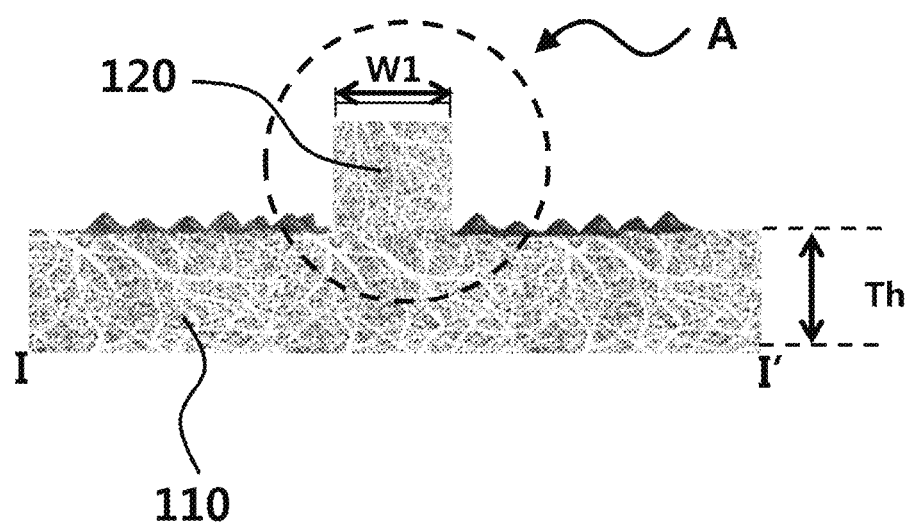

[Figure 3]
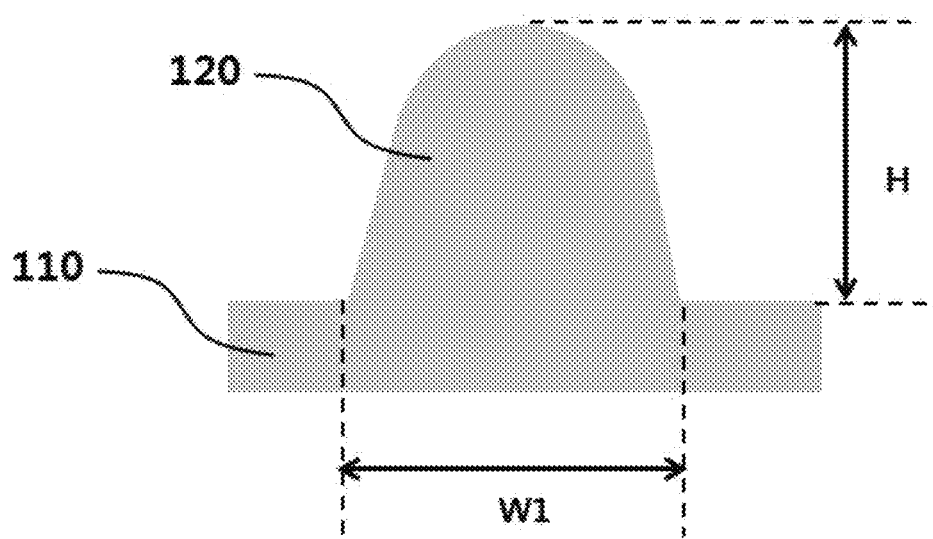
[Figure 4]
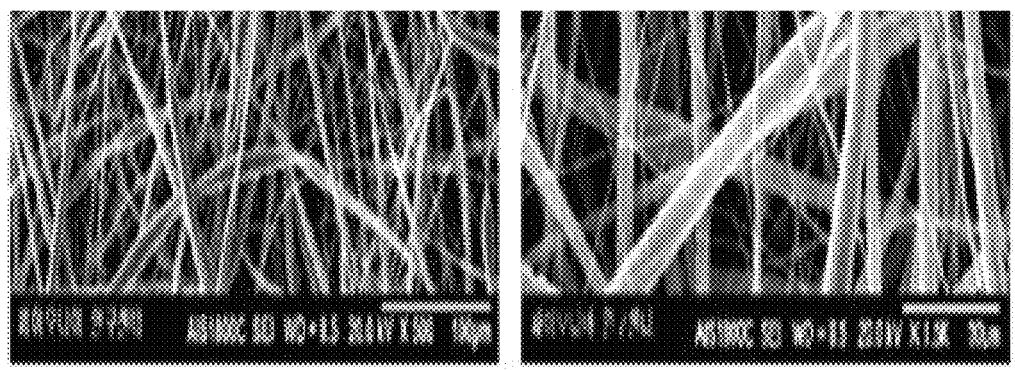

[Figure 5]
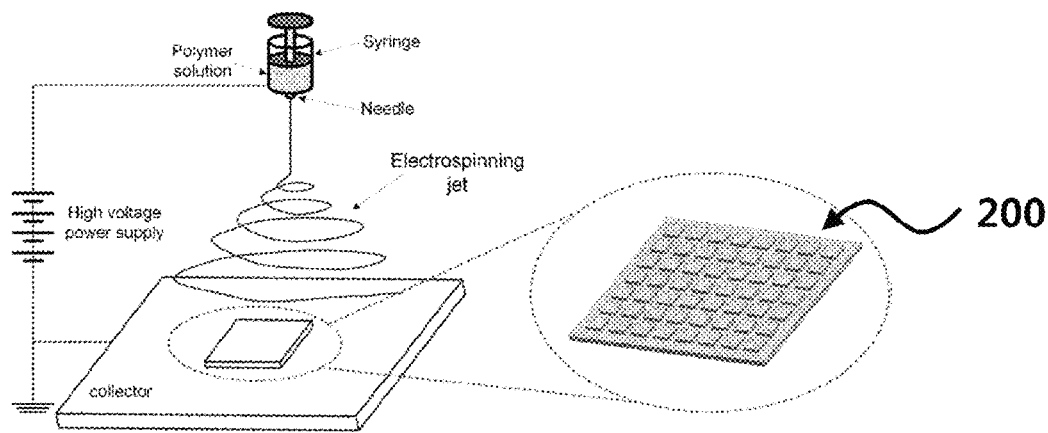
[Figure 6]
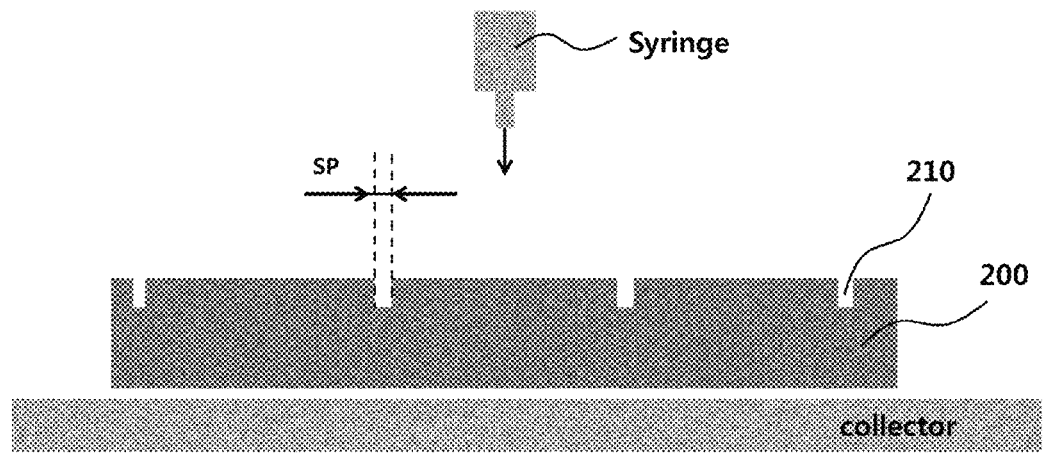

[Figure 7]
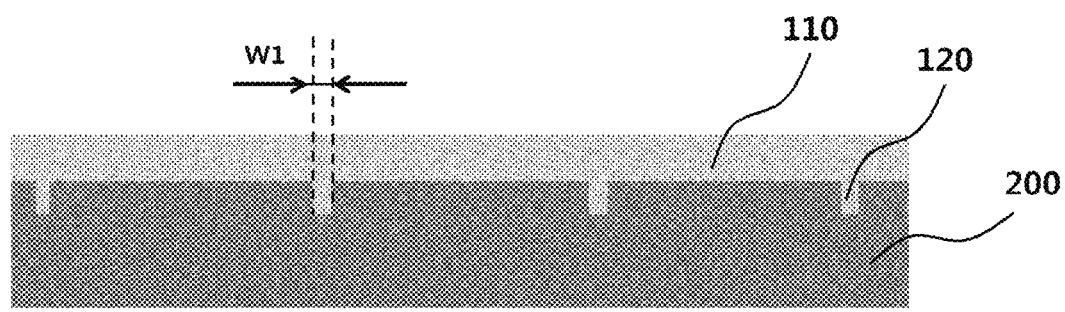
[Figure 8]
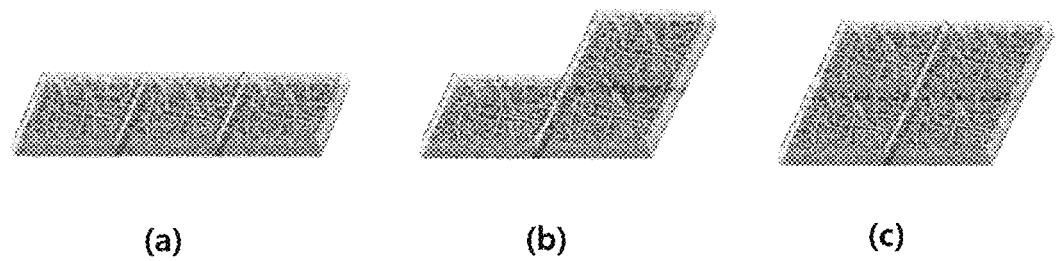
(a)          (b)          (c)

[Figure 9]
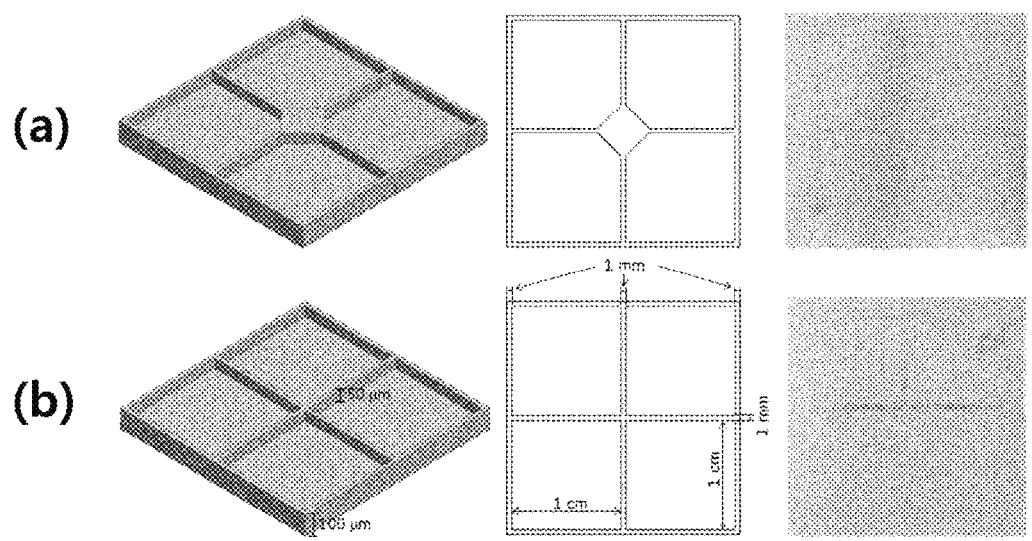
[Figure 10]
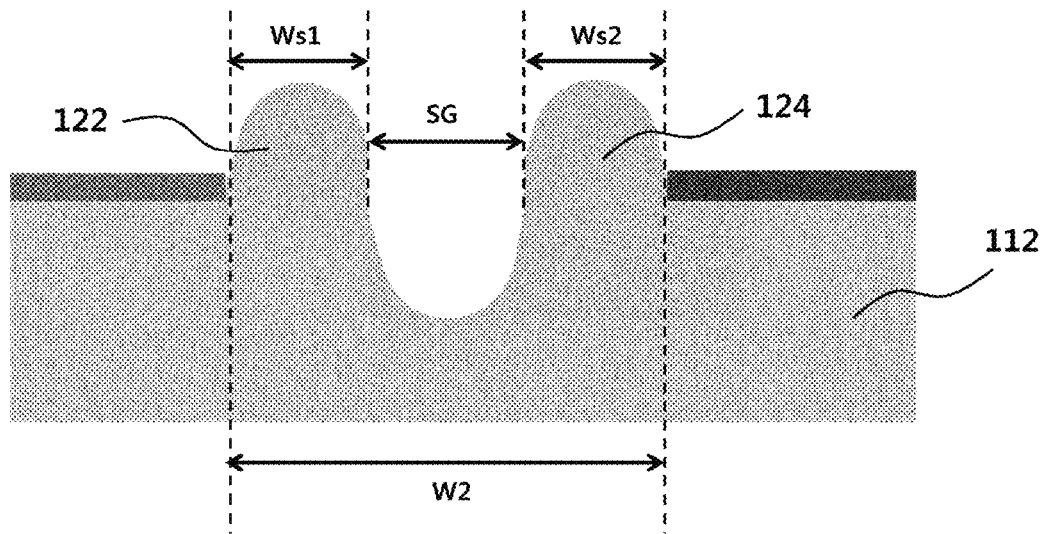

[Figure 11]
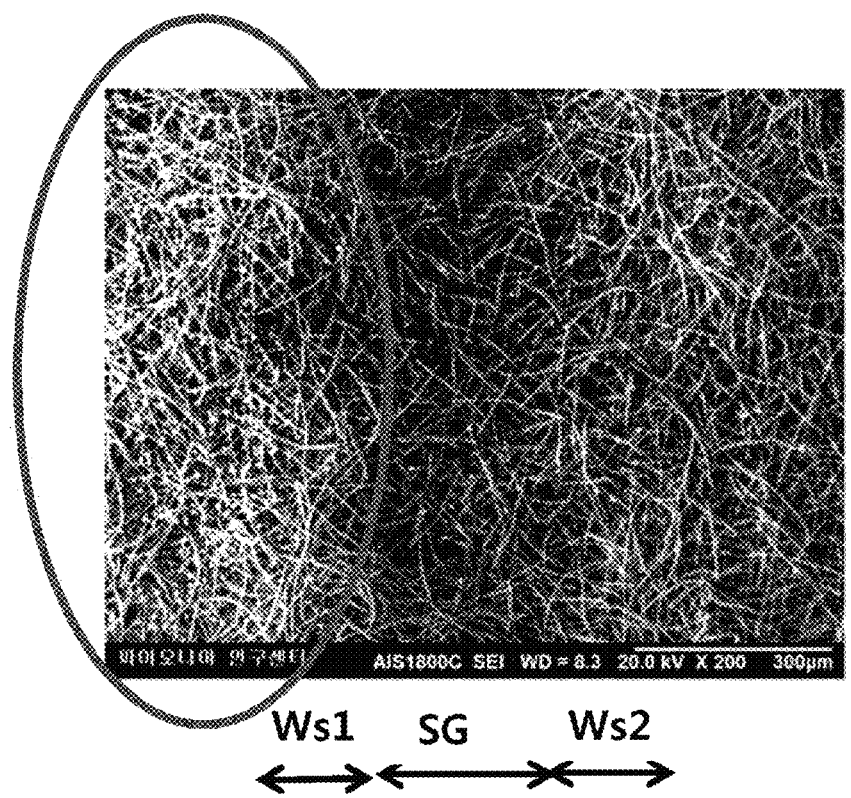

[Figure 12]
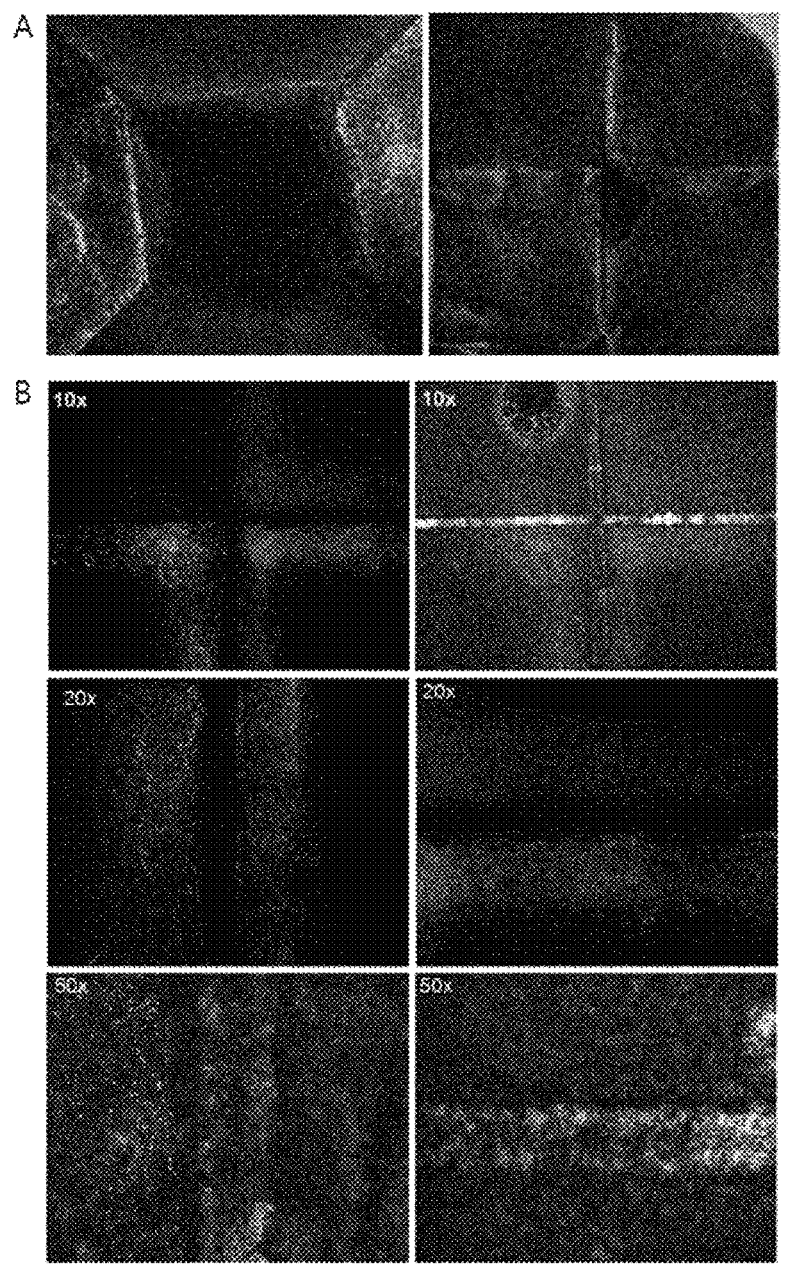

[Figure 13]
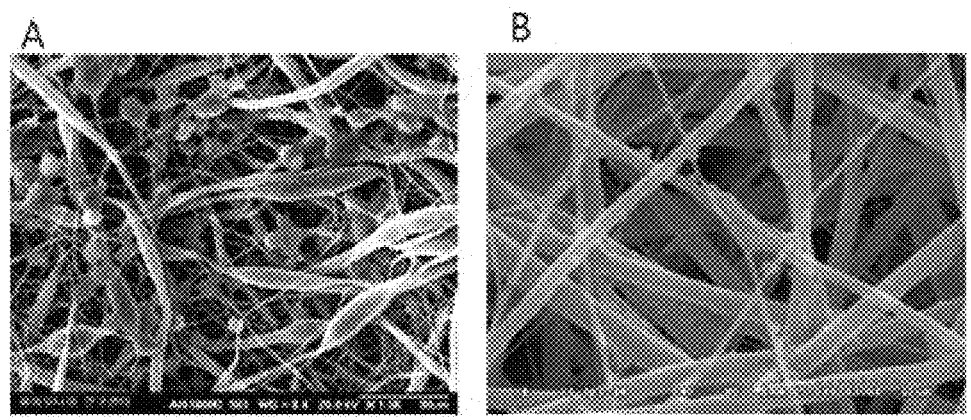

[Figure 14]
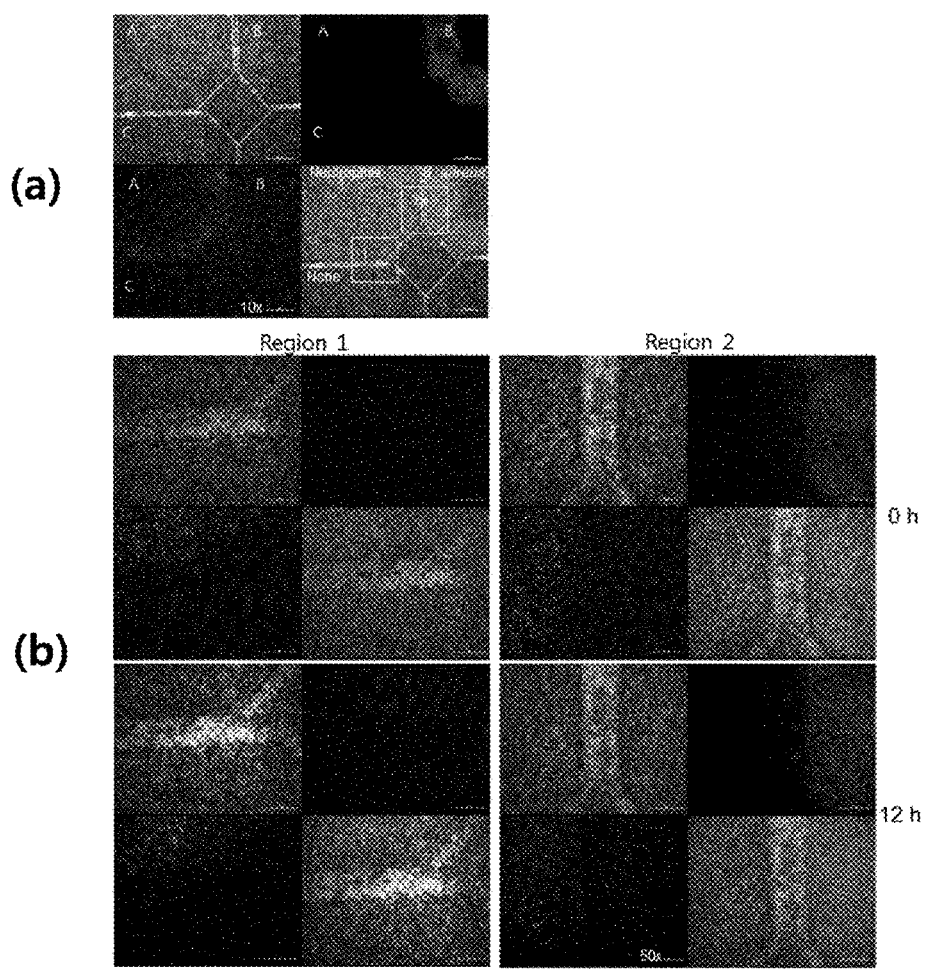

NANOFIBER STRUCTURE FOR CELL CULTURE, METHOD FOR MANUFACTURING THE NANOFIBER STRUCTURE, AND CELL ANALYSIS DEVICE INCLUDING THE NANOFIBER STRUCTURE

TECHNICAL FIELD

The present disclosure relates to a nanofiber structure for cell culture, a method for manufacturing the structure, and a cell analysis device including the nanofiber structure for cell culture. More particularly, the present disclosure relates to a nanofiber structure for cell culture compartmentalized to include at least two culturing regions, a method for manufacturing the structure, and a cell analysis device including the nanofiber structure for cell culture.

RELATED ART

Cell migration plays an important role in the development of various diseases. Cell migration occurs via a number of cellular processes. Cell migration may typically include cell invasion, chemotaxis, and haptotaxis. Immune cells recognize a concentration gradient of a chemotactic factor and move temporally and spatially based on the recognition.

In cell culture, migration of cells such as immune cells may be measured by the following methods: Boyden chamber assay, migration gap closure assay, Dunn chemotaxis chamber assay, under-agarose assay, time-lapse video microscopy assay, etc. However, these methods measure merely two-dimensional cell migration. In those methods, measuring the cell migration is based on an end-point, making it difficult to measure the cell migration in real-time. For real-time measurement, a large number of assays are required.

Since a tissue structure affects gene expression patterns and cell function, biomimetic systems should be developed to measure effects between various factors such as genotype, phenotype, and cell-extrinsic factors. A three-dimensional culture system may also be used for high-throughput experiments. For a three-dimensional culture system, spheroid culture, hanging drop culture, extracellular matrix gel culture, scaffold culture and the like are being developed. In vitro studies have mainly been done using two-dimensional or three-dimensional spheroids. However, the above systems show a large result difference from that in in vivo.

The scaffold culture is a technique for culturing cells in a scaffold having pores which is made using a natural/synthetic polymer. The three-dimensional culture scaffold should be constructed to enable oxygen transfer, nutrient transfer, and cell migration in addition to cell attachment. Korean Patent No. 10-1446687 discloses a three-dimensional cell culture using a nanofiber support. In this patent document, in order to cultivate two or more different cells in different regions, a bank is prepared with plastic or polydimethylsiloxane (PDMS). A thus-formed structure is used as an essay chip. In this connection, there is a need for assembly or technical supplement against leakage of culture fluid. Further, there is a need for a technique to overcome the disadvantage that gaps between fractions containing each cell are different at the nanoscale.

Furthermore, fabricating micropatterning by applying lithography or mechanical micromachining to an electrospun nanofiber scaffold is a very difficult process. It has been reported to fabricate microchannels by applying femtosecond laser ablation to polycaprolactone (PCL) nanofiber layers based on nanofibers (Lee, et al., Ann Biomed Eng. 2011; 39 (12): 3031-3041). The microchannels were made 100 μm wide, 100 μm deep, and 10 mm long. When smooth muscle cells were injected into the microchannel using a micro-pump, the cells are well distributed within the microchannels. There is no clogging of the microchannel with the cells. Although the microchannel has been developed as a technique that is used as a blood vessel model, these microchannels have limitations in culturing many kinds of cells.

In another technique for fabricating micropatterning nanofibers, microwells are made using a PDMS template and then, nanofibers and hydrogels are attached to the wells to produce micropatterned nanofibers (Song et al., Applied Materials Interface, 2014; 6 (10): 7034-7044). In this case, the nanofibers are present in the microwells, and, thus, the cells are liable to adhere to the wells, and, further, cell culture is realized in an encapsulation manner. However, this technique has complicated manufacturing processes.

PRIOR ART DOCUMENT

Patent Literature (Patent Document 1) 1. Korean Patent No. 10-1446687
(Patent Document 2) 2. Korean Patent No. 10-0953366
(Patent Document 3) 3. Korean Patent No. 10-0968231

Non-Patent Literature (Non-patent literature 1) Lee et al., Fabrication of patterned nanofibrous mats using a direct-write electrosinning, Langmuir, 2012; 28(18): 7267-7275
(Non-patent literature 2) Lee et al. Vascular wall engineering via femtosecond laser ablation: scaffolds with self-containing smooth muscle cell populations. Ann Biomed Eng. 2011; 39(12): 3031-3041.
(Non-patent literature 3) Song et al. Nanofibrous microposts and microwells of controlled shapes and their hybridization with hydrogels for cell encapsulation. ACS Appl. Mater. Interfaces, 2014; 6 (10): 7038-7044.

SUMMARY

Technical Purposes of Invention

One purpose of the present disclosure is to provide a nanofiber structure for cell culture, having a spacer with mass transfer channels, while being segmented into at least two or more culturing regions via the spacer.

Another object of the present disclosure is to provide a method for producing the nanofiber structure for cell culture with a simple process.

Another object of the present disclosure is to provide a cell analysis device comprising the nanofiber structure for cell culture.

Technical Solutions of Invention

In a first aspect, there is provided a nanofiber structure for cell culture, the structure comprising: a cell culture layer made of nanofibers; and a spacer protruding upward from a surface of the cell culture layer, wherein the spacer divides a region on the cell culture layer into at least two culturing regions, wherein the spacer is made of the same nanofibers as the cell culture layer and thus has a cell migration channel defined therein.

In one implementation of the first aspect, a lower end of the spacer is connected to the cell culture layer, wherein a width of the spacer decreases as the spacer extends from the lower end of the spacer to an upper end of the spacer. In one implementation of the first aspect, a width of a lower end of the spacer is larger than or equal to 100 μm and smaller than 1 mm.

In one implementation of the first aspect, the spacer has a double sub-spacer structure having two protrusions spaced apart from each other. In one implementation of the first aspect, the spacer includes a valley recessed from the surface of the cell culture layer and defined between the two protrusions.

In one implementation of the first aspect, a spacing between the two protrusions is 300 to 500 μm, wherein a bottom width of each of the protrusions is 200 to 400 μm.

In one implementation of the first aspect, a width of each of the protrusions decreases as each protrusion extends upwardly.

In one implementation of the first aspect, a nanofibers density in the cell culture layer is higher than the nanofibers density in the spacer.

In one implementation of the first aspect, the spacer extends in a form of a single closed curve along outer edges of the culturing regions.

In a second aspect, there is provided a method for manufacturing a nanofiber structure for cell culture, the method comprising: providing a mold, wherein the mold has at least two spaced portions divided by a recess defined in the mold; electrospinning nanofibers onto the mold such that the nanofibers cover the at least two spaced portions and fill the recess, thereby to form a nanofiber structure on the mold, wherein the nanofiber structure includes a cell culture layer having at least two culturing regions spaced via a spacer, wherein the nanofibers covering the at least two spaced portions of the mold define the at least two culturing regions respectively, wherein the nanofibers filling the recess defines the spacer, wherein the spacer is made of the same nanofibers as the cell culture layer and thus has a cell migration channel defined therein; and separating the nanofiber structure from the mold.

In one implementation of the second aspect, the method further comprises, before separating the nanofiber structure from the mold, heat-treating the nanofibers formed on the mold.

In one implementation of the second aspect, the spacer has a double sub-spacer structure having two protrusions spaced apart from each other, wherein the spacer includes a valley recessed from the surface of the cell culture layer and defined between the two protrusions. In one implementation of the second aspect, a width of the recess in the mold is larger than or equal to 1 mm and smaller than or equal to 2 mm.

In a third aspect, there is provided a cell analysis device comprising a nanofiber structure for cell culture, wherein the structure includes a cell culture layer made of nanofibers; and a spacer protruding upward from a surface of the cell culture layer, wherein the spacer divides a region on the cell culture layer into at least two culturing regions, wherein the spacer is made of the same nanofibers as the cell culture layer and thus has a cell migration channel defined therein, wherein the cell analysis device is configured to culture different cells in the at least two culturing regions respectively and to measure migration of the cells through the spacer.

Effects of Invention

According to the first to third aspects of the present disclosure, the nanofiber structure for cell culture includes at least two culturing regions, while the spacer is composed of the same nanofibers as the cell culture layer. Through the spacer with the mass transfer channel, intercellular migration or cell-generated molecules diffusion may be realized. Due to the formation of two or more culturing regions via the spacer(s), the nanofiber structure for cell culture according to the present disclosure may include two or more culturing regions. Thereby, the cell culture chambers capable of culturing two or more kinds of cells respectively at the same time may be realized.

This nanofiber structure for cell culture is provided in the cell analysis device for measurement and analysis of cell culture and/or cell migration. Thus, the movement of various kinds of cells may be measured in real time and at the same time. Thus, cell analysis may be performed in real time.

BRIEF DESCRIPTION OF THE DRAWINGS

FIG. 1 is a perspective view illustrating a nanofiber structure for cell culture according to one embodiment of the present disclosure.

FIG. 2 is a cross-sectional view taken along line I-I' of FIG. 1.

FIG. 3 is an enlarged view of a portion A of FIG. 2.

FIG. 4 is a photograph showing nanofibers constituting the nanofiber structure for cell culture in FIGS. 1 to 3.

FIGS. 5 to 7 are views for illustrating a method of manufacturing the nanofiber structure for cell culture as described in FIGS. 1 to 4.

FIG. 8 and FIG. 9 show a nanofiber structure for cell culture, which is different from FIG. 1.

FIG. 10 is a cross-sectional view illustrating a nanofiber structure for cell culture according to another embodiment of the present disclosure.

FIGS. 11 to 14 show photographs of cell culture samples 1 to 4.

DETAILED DESCRIPTIONS

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims. The same reference numbers in different figures denote the same or similar elements, and as such perform similar functionality.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a perspective view illustrating a nanofiber structure for cell culture according to one embodiment of the present disclosure. FIG. 2 is a cross-sectional view taken along line I-I' of FIG. 1.

Referring to FIG. 1 and FIG. 2, the nanofiber structure for cell culture 100 includes a cell culture layer 110 and a spacer 120.

The cell culture layer 110 may be formed of nanofibers and may have a layered three-dimensional matrix structure. Since the cell culture layer 110 is formed of nanofibers, the layer 110 has a very large effective surface area and high durability, and is easy to handle and is manufactured in various forms. Further, various substance may be easily chemically bonded to the cell culture layer 110.

The nanofibers constituting the cell culture layer 110 may be made of various materials such as synthetic polymers, biocompatible polymers, and the like. Examples of compounds that form nanofibers constituting cell culture layer 110 may include chitosan, elastin, hyaluronic acid, alginate, gelatin, collagen, cellulose, polyethylene glycol (PEG), polyethylene-oxide, polycaprolactone (PCL), polylactic acid (PLA), polyglycol acid (PGA), polylactic-co-glycolic acid, polyhydroxybutyreic-co-hydroxyvaleleic acid, polydioxanone, polylactidecaprolacton, polyesterurethan, polylactide-lactide, polyethylenevinylalcohol, polyacrylic acid, poly(vinyl alcohol), polyvinylpyrrolidone, polystyrene, polyaniline, etc. These may be used alone or in combination of two or more. The combination of two or more may be in the form of a copolymer or a simple mixture. Particularly, when the compound constituting the nanofibers is a biocompatible polymer, it contains a plurality of pores through which the cells can pass, thus facilitating attachment and culturing of cells thereon and thereto.

In one embodiment, the compound constituting the nanofibers may have a number average molecular weight of 10,000 to 1,000,000. For example, the number average molecular weight of the compound constituting the nanofibers may be 50,000 to 500,000.

For example, the diameter of each of the nanofibers may be in a range of about 100 nm to about 10 μm, and the cell culture layer 110 may be a single layer with the nanofibers randomly integrated with each other and having a thickness Th of about 50 to 70 μm.

The spacer 120 protrudes upward from the surface of the cell culture layer 110 and divides the cell culture layer 110 into at least two culturing regions. In this connection, spacer 120 is made of the same nanofibers as the cell culture layer 110 and has cell transfer channels. When cells are placed on each of the culturing regions, the cells may migrate between the two regions through the spacer 120. The cell transfer channels within the spacer 120 may be formed via the irregular integration between the nanofibers and the pores in the nanofibers themselves. In a plan view, the spacer 120 extends in one direction on the cell culture layer 110, delimiting both culturing regions. The space has a length extending in one direction and having a first width W1.

Hereinafter, the spacer 120 will be described in more detail with reference to FIG. 3 and FIG. 4 together with FIG. 1 and FIG. 2.

FIG. 3 is an enlarged view of a portion A of FIG. 2.

Referring to FIG. 3 with FIG. 1 and FIG. 2, a height H of the spacer 120 is defined as the distance from the surface of the cell culture layer 110 to the highest point of the spacer 120. The lower end of the spacer 120 is connected to the cell culture layer 110. The highest point defines the top of the spacer 120. The ratio between the height H of the spacer 120 and the thickness Th of the cell culture layer 110 may be in a range of about 1:1.2 to about 1:1.5. Preferably, when the ratio between the height H of the spacer 120 and the thickness Th of the cell culture layer 110 is 1:1, the nanofiber structure for cell culture 100 is structurally stable and cells are stably cultured in the culturing regions. For example, the height H of the spacer 120 may be in a range of about 50 μm to about 70 μm.

The first width W1 of the spacer 120 is defined as the bottom width of the spacer 120. From the bottom of the spacer 120 toward the top of the spacer, the width of the spacer 120 may gradually decrease. In particular, an apex portion of the top of the spacer 120 may have a round shape. In this connection, the height H of the spacer 120 may be substantially equal to the thickness Th of the cell culture layer 110 or smaller than the thickness Th of the cell culture layer 110.

On the first cell culture layer 110 adjacent to the spacer 120, first cells (shown in green) may be attached and cultured thereon. On the opposite second cell culture layer 110 adjacent to the spacer, second cells (shown in red) of a different species from the first cells may be attached and cultured thereon. In this connection, different first and second cultivating regions may be injected with different types of fluorescence-labeled cells.

For example, the first cell may be a disease cell or a bacterium, and the second cell may be an immune cell. By simultaneously culturing the first and second cells in one nanofiber structure for cell culture, it is possible to directly measure the migration and activity of the immune cells, and damage, death, and proliferation degrees of the disease cells. Using the color of the labeled fluorescence on each culturing region, cell migration may be easily observed with a fluorescence microscope.

In this connection, the immune cells may include neutrophils, macrophages, dendritic cells, NK cells, T cells, B cells, and the like. The immune cells may be human or mouse-derived cells. Specifically, the immune cells may be obtained by differentiating the cells isolated from the human blood or separated from the mouse bone marrow.

The disease cell may be a disease-induced cell, and may be a cancer cell. Examples of cancer cells may include liver cancer cells, colon cancer cells, stomach cancer cells, lung cancer cells, uterine cancer cells, breast cancer cells, thyroid cancer cells, pancreatic cancer cells, and the like. Alternatively, the bacteria may be *E. coli, Staphylococcus, Salmonella, shigella, Mycobacterium, Helicobacter pylori*, Yeast, Yellow mucus or tetanus.

FIG. 4 is a photograph showing nanofibers constituting the nanofiber structure for cell culture of FIG. 1 to FIG. 3.

Referring to FIG. 4 together with FIGS. 1 to 3, each of the cell culture layer 110 and the spacer 120 includes a matrix having a structure in which nanofibers are irregularly entangled with each other, as shown in an electron microscope photograph shown in FIG. 4. The left photograph shows a scale of 100 μm, while the right photograph shows a scale of 50 μm.

The density of the cell culture layer 110 is greater than the density of the spacer 120 with respect to the density at which the nanofibers are integrated with each other. That is, the density of the spacer 120 is lower than the density of the cell culture layer 110. As a result, the cell migration path becomes wider within the spacer. Accordingly, when the same material flows in the spacer 120 and the cell culture layer 110, the material may be rapidly moved in the spacer 120 with a wider mass transfer channel as compared to the cell culture layer 110. This difference in density may be achieved by forming the nanofiber structure for cell culture 100 via electrospinning nanofibers using a mold 200 (see FIGS. 5 and 6).

Hereinafter, with reference to FIGS. 5 to 7, a method of manufacturing the nanofiber structure for cell culture 100 described in FIGS. 1 to 4 will be described in detail.

FIGS. 5 to 7 are views for illustrating the method of manufacturing the nanofiber structure for cell culture described in FIGS. 1 to 4.

First, referring to FIG. 5, the nanofiber structure for cell culture 100 is manufactured using an electrospinning device. In an electrospinning device, while a syringe containing a polymer solution injects a polymer solution through a needle on a mold, the device applies an electric field between the syringe and a collector to conduct an electrospinning jet. This allows nanofibers to be integrated on the mold on the collector. In this connection, the electrospinning is carried out with the mold 200 being disposed on the collector.

The mold 200 has a counter shape opposite to that of the nanofiber structure for cell culture 100 to be produced. The mold 200 includes a recess 210 that is recessed therein from the surface thereof. A portion protruding relative to the recess 210 is defined as a convex portion. The recess 210 corresponds to the spacer 120 of the nanofiber structure for cell culture 100. The cell culture layer 110 covering the entire surface of the mold 200 may be connected to the spacer 120. The width SP of the recess 210 may be substantially the same as the bottom width W1 of the spacer 120. When the width SP of the recess 210 is greater than or equal to 100 μm and smaller than 1 mm, the nanofiber structure for cell culture 100 as described in FIGS. 1 to 4 may be formed.

The mold 200 may be made of silicon, quartz, ceramic, alumina, titania, glass, etc. The mold 200 may be fabricated as a silicon wafer using conventional wet and/or dry etching processes. In addition, the mold 200 having the concavo-convex pattern may be manufactured by using the aluminum thin film and the aluminum tape. When the mold 200 is formed of a conductive material, the electrospinning process may be performed by applying an electric field between the mold 200 and the syringe without using a separate collector.

Referring to FIGS. 5 and 6, the electrospinning process is performed with the mold 200 placed on the collector. By adjusting the concentration of the polymer solution, application voltage, and injection distance in the electrospinning process, the diameter, pore size, and integration density of the nanofibers may be controlled.

Referring to FIG. 7, using the electrospinning process, the nanofibers are integrated in the recess 210 in the mold 200, and the nanofibers are also integrated on the surface of the mold 200. The spacer 120 is formed corresponding to the recess 210. A cell culture layer 110 having a lamellar structure covering the entire mold 200 is formed. In this connection, the bottom width W1 of the spacer 120 may be substantially equal to the width SP of the recess 210. However, the upper end of the spacer 120 filled in the recess 210 is formed to be narrower than the lower end of the spacer 120. In this way, the recess 210 may not be completely filled. Further, the density of the nanofibers integrated on the surface of the mold 200 by electrospinning may be smaller than the density of the nanofibers integrated in the recess 210 by the electrospinning.

After the electrospinning process, heat treatment is performed with the mold 200 and the nanofibers structure 100 joined together. After the heat treatment process, the nanofibers structure 100 is separated from the mold 200. In this way, the nanofibers structure 100 illustrated in FIGS. 1 to 4 may be produced. The heat treatment process may be performed at 50° C. to 70° C.

In one example, although not shown in FIGS. 1 to 7, the nanofiber structure for cell culture 100 may be disposed on a base as a support. In this connection, a polymer coating layer may be disposed between the base support and the cell culture layer 110. The polymer coating layer may increase the adhesion between the nanofiber structure for cell culture 100 and the base. Examples of the material of the polymer coating layer may include polydimethylsiloxane (PDMS), polystyrene (PS), polymethyl methacrylate (PMMA), polytetrafluoroethylene (PTFE), polyethylene (PE), polyurethane (PU), cellulose, silicone rubber, and the like. For example, the polymer coating layer may be coated on the base by spin coating. The material of the polymer coating may be substantially the same material as the nanofibers constituting the nanofiber structure for cell culture 100. The polymer coating layer may be a thin film uniformly formed on the base. Each of the cell culture layer 110 and the spacer 120 has a structure in which nanofibers form a matrix.

FIG. 8 and FIG. 9 show the nanofiber structure for cell culture, which is different from FIG. 1.

FIG. 8 and FIG. 9 show the nanofiber structure for cell culture containing at least three or more culturing regions. As in FIGS. 8A, 8B and 8C, the spacers may extend in one direction or in two different directions. Thus, the nanofiber structure for cell culture including a plurality of culturing regions may be formed. Such a nanofiber structure for cell culture having a plurality of culturing regions may be provided in a cell analysis device. In this way, the device may be used to observe the movement of several species of cells at the same time, and conduct many experiments simultaneously for the same species.

Referring to FIG. 9, the spacer may extend into the shape of a single closed curve along the outer edge of the culturing region to delimit the culturing region. FIGS. 9A and 9B show the structure with 4 culture chambers as four culturing regions. The spacer is arranged in the shape of a single closed curve along the outer edges of the culturing regions. As shown in FIG. 9B, the width of the spacer may be uniformly formed in all portions thereof. As shown in FIG. 9A, the width of the intersection at which the spacers intersect may have a relatively large width as compared to remaining portions of the spacer. FIG. 9 shows a structure divided into four culturing regions. However, it is possible to design various nanofibers structures having at least two culturing regions by controlling the design of spacer 120.

The manufacturing method of the nanofiber structure for cell culture shown in FIGS. 8 and 9 is substantially the same as the manufacturing method as described in FIGS. 5 to 7. Thus, a detailed description thereof will be omitted.

FIG. 10 is a cross-sectional view illustrating a nanofiber structure for cell culture according to another embodiment of the present disclosure.

The nanofiber structure for cell culture shown in FIG. 10 is substantially the same as that described in FIGS. 1 to 4 except for a structure of the spacer. Therefore, redundant detailed descriptions therebetween will be omitted and only differences therebetween will be described.

Referring to FIG. 10 with FIG. 1, the spacer 120 includes two protrusions 122 and 124 spaced apart from each other and a valley between them. The two protrusions 122 and 124 each protrude from the surface of the cell culture layer 112, while the valley is recessed down to the surface of the cell culture layer 112. Around the valley, two protrusions are defined, namely a first protrusion 122 and a second protrusion 124. Each of the first and second protrusions 122 and 124 is formed such that the bottom widths Ws1 and Ws2 thereof are larger than the top widths thereof, as described in FIG. 3. The width thereof gradually decreases from the bottom to the top thereof. The bottom width Ws1 and Ws2 of each of the first and second protrusions 122 and 124 may be in a range of about 200 to about 400 µm. The width of the valley, which is the separation distance SG between the first and second protrusions 122 and 124, may be in a range of about 300 and about 500 µm. The bottom width W2 of the spacer 120, which is the sum of the bottom widths Ws1 and Ws2 of the first and second protrusions 122 and 124 and the separation distance SG, may be about 1 mm or more. For example, the bottom width W2 of the spacer 120, including the two protrusions 122 and 124, may be greater than or equal to 1 mm and smaller than or equal to 2 mm.

The two protrusions 122 and 124 serve as practical spacers for defining the culturing regions. The moving cells may be accumulated in the valley disposed between the protrusions. Thus, the movement of the cells may be more accurately confirmed from the valley portion. That is, the cells residing in one culturing region may pass through the first protrusion 122 and remain in the valley. Thus, the number of cells accumulated in the valley may be measured to analyze the mobility of the cells.

The spacer 120 with the two protrusions 122 and 124 and the valley may be formed by adjusting the width SP of the recess 210 in the mold 200 to 1 mm or more in the fabrication process using the electrospinning as described in FIGS. 5 to 7. When the width SP of the recess 210 is 1 mm or more, the nanofibers are not fully integrated within the recess 210 in the electrospinning process. That is, nanofibers are preferentially integrated on the edge of the recess 210. Thus, even within recess 210, there is a difference in nanofibers density. As the mold 200 and the nanofibers structure are separated from each other, the spacer 120 having a double sub-spacer structure including the two protrusions 122 and 124 and the valley may be formed. When the width of the spacer 120 is larger than 2 mm, it is relatively difficult to observe the movement of the cells. Therefore, the width of the spacer 120 is preferably 1 mm or larger and 2 mm or smaller.

According to the above description, the nanofiber structure for cell culture 100 includes at least two culturing regions, while the spacer 120 is composed of the same nanofibers as the cell culture layer 110. Through the spacer 120 with the mass transfer channel, intercellular migration or cell-generated molecules diffusion may be realized. Due to the formation of two or more culturing regions via the spacer(s) 120, the nanofiber structure for cell culture 100 according to the present disclosure may include two or more culturing regions. Thereby, the cell culture chambers capable of culturing two or more kinds of cells respectively at the same time may be realized. This nanofiber structure for cell culture 100 is provided in a cell analysis device for measurement and analysis of cell culture and/or cell migration. Thus, the movement of various kinds of cells may be measured in real time and at the same time. Thus, cell analysis may be performed in real time.

In the following, the present disclosure will be described in more detail through specific examples. The following examples are intended to illustrate embodiments of the present disclosure only, and the present disclosure is not limited thereto.

EXAMPLE

Production of Nanofiber Structure for Cell Culture (1) Production of Mold

An aluminum foil was prepared, and an aluminum tape was cut into square pieces. The tape pieces were attached in a matrix form on the aluminum foil so as to be spaced apart from each other. As a result, a region of the foil in which the aluminum tape is attached thereon is a convex region while a spaced region of the foil between the aluminum tapes is the concave region. Thus, a mold having such a structure has substantially the same structure as the mold 200 as described in FIGS. 5 and 6. In this connection, the width of the recess was 1 mm.

(2) Electrospinning Jet

The nanofibers were injected in an electrospinning manner toward the mold with the prepared mold being placed on the collector of the electrospinning device. The injection distance was 10 cm, and the applied voltage was 10 to 15 kV. In this connection, the electrospinning is performed by moving a biaxial-based stage so that the nanofibers on the mold may be injected on the mold with a uniform thickness. The nanofibers include polycaprolactone (PLC). The average diameter of each of the nanofibers was 500 nm.

(3) Heat Treatment and Separation

After the nanofibers were electrospun, the nanofibers were heat-treated at a temperature of about 60° C. for about 5 seconds in a state where the nanofibers were integrated in and on the mold. The heat-treated nanofiber structure for cell culture was separated from the mold. Accordingly, the nanofiber structure for cell culture according to one example of the present disclosure was prepared. The thickness of the cell culture layer of the fabricated nanofiber structure for cell culture was about 50 µm, and the spacer was formed to have a double sub-spacer structure. In the double sub-spacer structure, the height of each of the two protrusions was about 50 µm, the width of each protrusion was 300 µm, and the spacing between the protrusions was 400 µm (See FIGS. 10 and 11).

Cell Culture Sample 1

Dendritic cells were obtained by differentiating the bone marrow cells with granulocyte macrophage-colony stimulating factor (GM-CSF) and interleukin-4 (IL-4). Then, 10,000 of the dendritic cells thus-obtained were mixed in 10 µl of a phosphate buffered saline (PBS) solution to prepare a mixture. The mixture was placed in a culturing region of the nanofiber structure for cell culture as prepared as described above, and was left for 4 hours. The results are shown in FIG. 11.

FIG. 11 is an electron microscope graph of the cell culture sample 1. Referring to FIG. 11, dendritic cells were attached to the nanofibers in the left region of the cell culture layer adjacent to the spacer.

Cell Culture Sample 2

CT-26 cells, a colon cancer cell line, and dendritic cells used in the preparation of cell culture sample 1 were stained with PKH67 (green fluorescence) and PKH26 (red fluorescence), respectively. The CT-26 cells and dendritic cells (10,000) were mixed into 10 µl of the PBS to form a mixture. The mixture was placed in the culturing region of the nanofiber structure for cell culture prepared as described above, and was left for 4 hours. Fluorescence microscopy was used to measure results. The results are shown in A in FIG. 12.

At the same time, colorectal cancer cells were stained with red fluorescence and blue fluorescence together with dendritic cells stained with green fluorescence. Fluorescence-labeled cells were placed in the culturing regions of the nanofiber structure for cell culture as prepared as described above, and were left for 4 hours. Fluorescence microscopy was used to measure results. The results are shown in A in FIG. 12.

In FIG. 12, a left photo of A shows the green/red fluorescence while the right photo of A shows the green/blue/red fluorescence. These photographs show that colon cancer cells and dendritic cells are stably cultured in the nanofiber structure for cell culture.

Cell Culture Sample 3

Bone marrow cells were isolated from the mice and the dendritic cells were differentiated from the bone marrow cells. Except that the dendritic cells thus derived were used, cell culture sample 3 was prepared in substantially the same manner as in the preparation of cell culture sample 2. The dendritic cells were prepared as follows.

Bone marrow cells were isolated from thighs and calves of Balb/c mice at 5 to 6 weeks of age. The separated bone marrow cells ($1\times10^6$ cells/ml) were cultured in RPMI-1640 medium containing 10% fetal bovine serum, 100 U/ml penicillin, and 100 μg/ml streptomycin with 37° C. incubator receiving 10% $CO_2$. To induce differentiation into dendritic cells, bone marrow cells were cultured in the presence of 15 ng/ml of granulocyte macrophage colony stimulating factor (GM-CSF) and 15 ng/ml of interleukin-4 (IL-4) for 7 days. The differentiated dendritic cells are distinguished by using CD11c as a specific protein surface factor thereto, and major histocompatibility complex (MHC)-II. The distinguished dendritic cells were separated using anti-CD11c antibody-bound microbeads. The results are shown in B in FIG. 12. FIG. 12B shows fluorescence microscope photographs as taken at 10 times, 20 times, and 50 times magnification respectively.

It is confirmed referring to B in FIG. 12 that dendritic cells stained with green fluorescence and colorectal cancer cells stained with blue and red fluorescence are stably cultured in the culturing regions, respectively.

Cell Culture Sample 4

Neutrophils as immune cells were isolated from mice. *Staphylococcus aureus* was used as disease cells. Thus, cell culture sample 4 was prepared. The neutrophils were obtained in the following manner.

Three ml of 3% thioglycollate solution was injected into the peritoneum of Balb/c mice at 5 to 6 weeks of age using a 26G injection needle. After 6 hours, the cervical vertebra of the mouse was dislocated and the skin was peeled off. The peritoneum was cut with scissors, and the solution in the abdominal cavity was collected using a Pasteur pipette. The red blood cell lysis solution was added by 2 ml to samples and was mixed to react for 2 minutes. Then, the collected solution was centrifuged at 1700 rpm at 4° C. The cells after centrifugation were treated with 10 μl of biotin-conjugated Ly6-G antibody in 500 μl of Ethylene diamine tetraacetic acid (EDTA)-balanced salt solution (BSS) solution and were reacted at 4° C. for 20 minutes. EDTA-BSS solution was added thereto, followed by centrifugation. Again, the resulting product were treated with 10 μl of biotin-conjugated microbeads in 500 μl of EDTA-BSS solution and reacted at 4° C. for 20 minutes. Neutrophils bound to the microbeads were isolated using MS column of MACS.

*Staphylococcus aureus* was cultured and grown in LB medium.

Neutrophils and bacteria were fluorescently stained with PKH67 and PKH26, respectively. An electron micrograph showing the state of attaching the fluorescent-stained neutrophil and bacteria to the nanofibers structure is shown in FIG. 13. An electron micrograph showing the state that the fluorescently-stained neutrophils and bacteria were attached to the nanofibers structure after being left for 12 hours is shown in FIG. 14.

In FIG. 13, A is a photograph with the neutrophils being attached to the present fiber structure and B is a photograph with staphylococci being attached to the present fiber structure. FIG. 13 shows that immune cells and bacteria are stably attached to the nanofibers in the corresponding culturing regions.

FIG. 14 is directed to the nanofibers structure including the A, B, and C culturing regions. In FIG. 14, in an inset (a), neutrophils are attached to A region, staphylococci are attached to B and C regions. In a right bottom portion of the inset (a), a region between A and C is defined as region 1 and the region between A and B is defined as region 2. The upper two photographs of an inset (b) show the regions 1 and 2, respectively. The lower two photographs of an inset (b) show the regions 1 and 2, respectively after 12 hours.

Referring to the inset (b) in FIG. 14, it may be seen that, after 12 hours, the neutrophils migrate into the spacer placed between the two culturing regions. Thus, it may be seen that the movement of the cells may be observed with a fluorescence microscope over time using the nanofibers structure according to the present disclosure.

In the above description, numerous specific details are set forth in order to provide a thorough understanding of the present disclosure. The present disclosure may be practiced without some or all of these specific details. Examples of various embodiments have been illustrated and described above. It will be understood that the description herein is not intended to limit the claims to the specific embodiments described. On the contrary, it is intended to cover alternatives, modifications, and equivalents as may be included within the spirit and scope of the present disclosure as defined by the appended claims.

What is claimed is:

1. A nanofiber structure for cell culture, the structure comprising:
    a cell culture layer made of nanofibers; and
    a spacer protruding upward from a surface of the cell culture layer, wherein the spacer divides a region on the cell culture layer into at least two culturing regions, wherein the spacer is made of the same nanofibers as the cell culture layer and thus has a cell migration channel defined therein.

2. The nanofiber structure of claim 1, wherein a lower end of the spacer is connected to the cell culture layer, wherein a width of the spacer decreases as the spacer extends from the lower end of the spacer to an upper end of the spacer.

3. The nanofiber structure of claim 2, wherein a width of a lower end of the spacer is larger than or equal to 100 μm and smaller than 1 mm.

4. The nanofiber structure of claim 1, wherein the spacer has a double sub-spacer structure comprising two protrusions spaced apart from each other.

5. The nanofiber structure of claim 4, wherein the spacer comprises a valley recessed from the surface of the cell culture layer and defined between the two protrusions.

6. The nanofiber structure of claim 4, wherein a spacing between the two protrusions is 300 to 500 μm, wherein a bottom width of each of the protrusions is 200 to 400 μm.

7. The nanofiber structure of claim 4, wherein a width of each of the protrusions decreases as each protrusion extends upwardly.

8. The nanofiber structure of claim 1, wherein a nanofiber's density in the cell culture layer is higher than the nanofiber's density in the spacer.

9. The nanofiber structure of claim 1, wherein the spacer extends in a form of a single closed curve along outer edges of the culturing regions.

10. A method for manufacturing a nanofiber structure for cell culture, the method comprising:

providing a mold, wherein the mold has at least two spaced portions divided by a recess defined in the mold;

electrospinning nanofibers onto the mold such that the nanofibers cover the at least two spaced portions and fill the recess, thereby to form a nanofiber structure on the mold, wherein the nanofiber structure includes a cell culture layer having at least two culturing regions spaced via a spacer, wherein the nanofibers covering the at least two spaced portions of the mold define the at least two culturing regions respectively, wherein the nanofibers filling the recess defines the spacer, wherein the spacer is made of the same nanofibers as the cell culture layer and thus has a cell migration channel defined therein; and separating the nanofiber structure from the mold.

11. The method of claim 10, wherein the method further comprises, before separating the nanofiber structure from the mold, heat-treating the nanofibers formed on the mold.

12. The method of claim 10, wherein the spacer has a double sub-spacer structure comprising two protrusions spaced apart from each other, wherein the spacer comprises a valley recessed from the surface of the cell culture layer and defined between the two protrusions.

13. The method of claim 12, wherein a width of the recess in the mold is larger than or equal to 1 mm and smaller than or equal to 2 mm.

14. A cell analysis device comprising a nanofiber structure for cell culture, wherein the structure comprises a cell culture layer made of nanofibers; and a spacer protruding upward from a surface of the cell culture layer, wherein the spacer divides a region on the cell culture layer into at least two culturing regions, wherein the spacer is made of the same nanofibers as the cell culture layer and thus has a cell migration channel defined therein, wherein the cell analysis device is configured to culture different cells in the at least two culturing regions respectively and to measure migration of the cells through the nanofiber spacer.

* * * * *